United States Patent [19]
Ayabe et al.

[11] Patent Number: 4,549,028
[45] Date of Patent: Oct. 22, 1985

[54] PROCESS FOR THE PREPARATION OF HYDANTOIN PRECURSOR OF PHENYLALANINE

[75] Inventors: Mitsukuni Ayabe; Tunehiko Shimizui; Iwao Kibayashi; Hideki Hirano, all of Tokyo, Japan

[73] Assignee: Denki Kagaku Kogyo Kabushiki Kaisha, Tokyo, Japan

[21] Appl. No.: 552,288

[22] Filed: Nov. 16, 1983

[30] Foreign Application Priority Data

Apr. 22, 1983 [JP] Japan .................. 58-70147

[51] Int. Cl.$^4$ ........................... C07D 233/74
[52] U.S. Cl. .................... 548/308; 562/443
[58] Field of Search ........................ 548/308

[56] References Cited

U.S. PATENT DOCUMENTS 3,752,821  8/1973  Wollner et al. .............. 548/308

OTHER PUBLICATIONS

Roger Gaudry, Can. J. Res., 26 (B), 773–776 (1948).

Primary Examiner—Richard A. Schwartz
Attorney, Agent, or Firm—Albert L. Jeffers; Stephen T. Belsheim

[57] ABSTRACT

A precursor of phenylalanine containing as a major component 5-benzylhydantoin is prepared by reacting, in an aqueous medium, a bisulfite addition salt of phenylacetaldehyde with cyanide and carbonate ions, each being in a molar ratio of equimol or more to said bisulfite addition salt and ammonium ion in a molar ratio of 2 or more to said carbonate ion.

The thus prepared precursor of phenylalanine may be converted into phenylalanine by a hydrolysis under a basic or acidic condition.

4 Claims, No Drawings

… …

PROCESS FOR THE PREPARATION OF HYDANTOIN PRECURSOR OF PHENYLALANINE

BACKGROUND OF THE INVENTION

This invention relates to a commercially advantageous process in accordance with which a precursor of phenylalanine can be prepared with a high yield.

L-Phenylalanine is a nutrient, one of essential amino acids, and often used in for infusion solutions. Also, it has an important use as an intermediate for synthesis of L-aspartyl phenylalanine methylester, which is one of the artificial sweeteners.

It is well-known in the art that L-phenylalanine is prepared by an optical or racemic resolution of DL-phenylalanine (hereinunder referred to as phenylalanine), which is in turn prepared by way of a synthetic method using phenylacetaldehyde as a starting material. The phenylacetaldehyde, however, is expensive and, as it is, thermally or chemically unstable, so that the handling in a commercial scale is difficult.

On the other hand, bisulfite addition salts of phenylacetaldehyde may be used as the starting material for synthesis of phenylalanine and the pure compound thereof is commercially easy-to-handle powders.

The phenylacetaldehyde has, hitherto, been produced industrially by an isomerization reaction of styrene oxide, while lower-cost processes of the production are progressively developed using direct oxidation of styrene, hydrolysis of $\beta,\beta$-dihaloethylbenzene, a hydroformylation reaction of benzyl halide and the like.

In these processes, the most effective way of recovering pure phenylacetaldehyde from the reaction system may be carried out by a contact treatment of the reaction solution with bisulfite or its solution followed by separation and recovery of phenyl acetaldehyde as the bisulfite addition salt. Therefore, such a bisulfite addition salt of phenylacetaldehyde is considered as an important starting material for synthesis of phenylalanine.

It is also known in the art that 5-benzylhydantoin, precursor of phenylalanine, is synthesized from a bisulfite addition salt of phenylacetaldehyde (Gaudry; Canadian Journal of Research, vol. 26(B) p.p 773~776 (1948)). In this synthesis, 5-benzylhydantoin with low yield, that is 42% or so, is obtained by reacting in a 50% aqueous solution of ethanol a 1:2:4 mixture of a bisulfite addition salt of phenylacetaldehyde, potassium cyanide and ammonium carbonate.

SUMMARY OF THE INVENTION

It is an object of this invention to provide a process for preparing a precursor of phenylalanine in which the precursor can be obtained with a commercially high yield.

It is another object of this invention to raise the yield of the phenylalanine precursor containing as a major component 5-benzylhydantoin, which is synthesized from a bisulfite addition salt of phenylacetaldehyde.

These objects of this invention may be attained by a process for the preparation of a precursor of phenylalanine containing as a major component 5-benzylhydantoin, which comprises reacting in an aqueous medium, a bisulfite addition salt of phenylacetaldehyde with cyanide and carbonate ions, each being in a molar ratio of equimol or more based on said bisulfite addition salt and ammonium ion in a molar ratio of 2 or more based on said carbonate ion.

One of the particular features of this invention resides in the aspect that the reaction is carried out in such a system that ammonium ions or free ammonia is allowed to exist in the reaction system in a higher amount than the amount of ammonium ion corresponding to ammonium carbonate.

DETAILED DESCRIPTION OF THE INVENTION

The bisulfite addition salt of phenylacetaldehyde to be used as a starting material in the process according to this invention is generally sodium or potassium bisulfite addition salt, which may be supplied to the reaction system in the form of crystalline powders or in the form dissolved or suspended in an appropriate liquid medium. Such a liquid medium may generally be water, however, any other medium which does not inhibit the reaction may be used in this invention.

The source of cyanide ions employed in this invention may be any materials able to generate cyanide ions. Illustrative examples of the source are hydrogen cyanide, sodium cyanide, potassium cyanide and ammonium cyanide. The molar ratio of the cyanide ion source to the bisulfite addition salt is equimol or more, preferably about 1.1. Even if the cyanide ion is used in a large amount, it hardly contributes to the increase of the yield of end product and tends to generate colored materials originating from polymerization of cyanide ions.

The source of carbonate ions employed in this invention may be any materials able to generate carbonate ions and exemplified by ammonium carbonate, sodium carbonate, potassium carbonate, ammonium hydrogen carbonate, sodium hydrogen carbonate, potassium hydrogen carbonate and the like. The molar ratio of the carbonate ion to the bisulfite addition salt of phenylacetaldehyde is equimol or more, preferably 1.1 to 3.

The source of ammonium ions employed in this invention may be any ammonium compounds and exemplified by ammonia, ammonium hydroxide, ammonium carbonate, ammonium hydrogen carbonate and ammonium sulfate. The molar ratio of the ammonium ion to the carbonate ion supplied to the reaction system is 2.0 or more, preferably 2.5 or more, more preferably 3 to 7. Among these compounds, aqueous solutions of ammonia and ammonium hydroxide are useful as the source to exist in a molar ratio of 2 or more. When the concentration of ammonium ions in an aqueous medium is increased, the ammonium ions tend to yield free ammonia. But this phenomenon should not by no means adversely affect the reaction system.

When the excessive ammonium ions or free ammonia as the case may be, exists in the reaction system, the yield of precursor of phenylalanine including as a major component 5-benzylhydantoin apparently increases as compared with the above-mentioned Gaudry method. This effect owes to the increase of solubilities of cyanhydrine, aminonitrile and the like existing as intermediates in the preparation of the phenylalanine precursors, in the aqueous medium.

The aqueous reaction medium used in this invention may preferably be water. The amount of water to be used is not limited to any extent, however, preferably is two to twenty times in weight as much as the bisulfite addition salt of phenylacetaldehyde. There may also be used in the reaction system hydrophylic organic solvents such as methanol and ethanol to be mixed with water.

The order of mixing these starting materials and mediums may freely be chosen. They may be mixed and heated under an ambient pressure or a pressurized condition.

The reaction temperature may be chosen from the range between 50° to 150° C., preferably 70° to 100° C. The reaction time may be chosen, in consideration of the reaction temperature or other reaction conditions, from the range of 15 minutes to 20 hours, preferably 30 minutes to 10 hours.

The reaction is carried out under stirring and in the batch or continuous process.

The thus prepared precursor according to this invention includes 5-benzylhydantoin as a major component, amide $\beta$-phenyl-$\alpha$-ureidopropionate, and in some conditions a small amount of phenylalanine, $\beta$-phenyl-$\alpha$-aminopropionitrile and the like. All of these products may be used as precursor of phenylalanine. The precursor according to this invention, therefore, is obtained mostly as a mixture of these precursor materials and such a mixture as it is may be led to phenylalanine by hydrolysis under a basic or acidic condition without separating any of each material. The hydrolysis of the precursors may be carried out by using conventional methods in the presence of an acid such as hydrochloric acid and sulfuric acid, or a base of metal hydroxide such as of alkali metals and alkaline earth metals. The residual carbonate ions and ammonium ions in the reaction system sometimes change into carbon dioxide gas and ammonia gas owing to the addition of the acid or base. These gases, however, may be removed from or retained in the reaction system at the start of hydrolysis.

It is the fact that some increase of the temperature of hydrolysis reaction enables shortage of the reaction time. The reaction may be completed at 100° C. within 3 to 5 hours under ambient pressure or at 150° C. to 200° C. within several to several decades minutes under a pressurized condition to give phenylalanine with high yield.

In a commercial scale, the precursor thus obtained in the process according to this invention, as it is, may be supplied without separating each component to the hydrolysis procedure.

When the hydrolysis of the precursor is complete, volatiles such as ammonia may be removed and recovered from the reaction product mixture by heating or condensing the mixture and the phenylalanine crystals may be obtained by neutralizing and filtering the residual mixture.

In accordance with this invention, the bisulfite addition salt of phenylacetaldehyde which can easily be handled and low priced, may be used as a starting material to obtain phenylalanine with high yield having important uses such as an intermediate of the synthesis of L-aspartyl phenylalanine methylester, one of useful artificial sweetners.

This invention is further described in detail by the following non-limitative Examples and Comparative Examples.

EXAMPLE 1

Into a stainless steel-made reactor having a volume of 100 l were charged 6.72 kg (30 mol) of sodium bisulfite addition salt of phenylacetaldehyde, 1.76 kg (35.9 mol) of sodium cyanide, 3.46 kg (36.0 mole) of ammonium carbonate, 6.0 l (90 mole) of a 25% aqueous solution of ammonia and 35 l of water and the mixture was reacted under stirring at 80° C. for four hours.

After completion of the reaction the resulting free ammonia was removed by heating the reaction mixture. The mixture was thereafter cooled to room temperature to obtain crystals, which were then collected by filtration and dried. Yield: 5.12 kg.

The thus obtained crystals were identified by high performance liquid chromatography as a mixture of 93.0% of 5-benzylhydantoin, 3.2% of amide hydantoate, 0.6% of hydantoic acid and 0.9% of phenylalanine. (The yield of 5-benzylhydantoin calculated based on the amount of sodium bisulfite addition salt of phenylacetaldehyde used was 83.5%).

Comparative Example 1

The reaction was carried out in the same manner as in Example 1, except that 25% aqueous ammonia was not added to the reaction mixture. After completion of the reaction the reaction product mixture was cooled and treated in the same manner as in Example 1 to obtain 0.95 kg of crystals.

The thus obtained crystals were identified by high performance liquid chromatography as a mixture of 90.9% of 5-benzylhydantoin, 2.8% of amide hydantoate, 0.8% of hydantoic acid and 0.8% of phenylalanine. (The yield of 5-benzylhydantoin calculated based on the amount of sodium bisulfite addition salt of used was 15.2%).

EXAMPLE 2

The reaction was carried out in the same manner as in Example 1. After completion of the reaction the resulting free ammonia was removed by heating the reaction mixture and 6.0 kg (150 mole) of caustic soda was added to the resulting mixture so as to carry out hydrolysis at 150° C. for 0.5 hour.

The hydrolyzed mixture was neutralized by using hydrochloric acid to crystallize phenylalanine. The thus formed crystals was collected by filtration. The filtrate was then condensed to crystalize phenylalanine, which was collected in the same manner as the above. The phenylalanine content of these crystals obtained was subjected to high performance liquid chromatography. As a result, the yield of phenylalanine calculated based on a bisulfite addition salt of phenyl acetaldehyde used was 91.3%. This result shows the fact that some precursors of phenylalanine other than 5-benzylhydantoin exist in the product of Example 1.

Comparative Example 2

The reaction was carried out in the same manner as in Comparative Example 1. After the reaction was complete, the hydrolysis was carried out at 150° C. for 0.5 hour by adding 6.0 kg (150 mole) of caustic soda to the reaction mixture.

The phenylalanine crystals were recovered in the same manner as in Example 2 and identified. The yield of phenylalanine calculated based on the amount of the sodium bisulfite addition salt of phenylacetaldehyde was 17.8%.

EXAMPLE 3

The same reaction procedure as in Example 2 was carried out using 6.72 kg of sodium bisulfite addition salt of phenylacetaldehyde, 1.76 kg of sodium cyanide, 3.46 kg of ammonium carbonate, 22 l of aqueous ammonia and 19 l of water to give 5.02 kg of phenylalanine crystals. The phenylalanine content of the thus obtained crystals was 95%. (The yield of phenylalanine calculated based on the amount of a sodium bisulfite addition salt of phenylacetaldehyde; 96.3%).

EXAMPLE 4

The reaction was carried out in the same manner as in Example 1, except that 31 l of water and 4 l of methanol were used. After completion of the reaction the resulting free ammonia and methanol were removed by heating the reaction solution which was thereafter cooled to room temperature to effect crystallization. The thus obtained crystals were then collected and identified. The yield of 5-benzylhydantoin was 85.1%.

In the above procedure, the final reaction solution including the crystals was subjected to hydrolysis at 190° C. for 0.5 hour using 6.0 kg (150 moles) of caustic soda. The thus hydrolyzed solution was thereafter treated in the same manner as in Example 2 to give phenylalanine crystals. The yield of phenylalanine calculated based on the amount of the sodium bisulfite addition salt of phenylacetaldehyde was 93.9%.

EXAMPLE 5

In a 100 l-volume hasteroi-made autoclave was placed 7.2 kg (30 moles) of a potassium bisulfite addition salt of phenylacetaldehyde, 1.76 kg (35.9 moles) of sodium cyanide, 4.32 kg (45 mole) of ammonium carbonate, 6 l (90 mole) of a 25% aqueous ammonia, 9 l of methanol and 24 l of water and the mixture was reacted at 100° C. for 2 hours to obtain precursors of phenylalanine. After the ammonia and methanol were removed by heating the reaction solution, the hydrolysis was carried out at 150° C. for 1.0 hour using 4.8 kg (120 moles) of caustic soda.

The phenylalanine crystals were obtained by treating the thus hydrolyzed solution in the same manner as in Example 2. The yield of phenylalanine calculated based on the amount of potassium bisulfite addition salt of phenylacetaldehyde was 90.2%.

What we claim is:

1. A process for the preparation of a mixture of precursors of phenylalanine containing as a major component 5-benzylhydantoin, which comprises reacting in an aqueous medium, a bisulfite addition salt of phenylacetaldehyde with cyanide and carbonate ions, each being in a molar ratio of equimol or more to said bisulfite addition salt and ammonium ions in a molar ratio of greater than 2 to said carbonate ion.

2. The process as set forth in claim 1, wherein said bisulfite addition salt of phenylalanine is sodium or potassium bisulfite addition salt.

3. The process as set forth in claim 1, wherein a source of said ammonium ions is ammonia, ammonium hydroxide, ammonium carbonate, ammonium hydrogen carbonate or ammonium sulfate.

4. The process as set forth in claim 1, wherein said reaction is carried out at 50°–150° C. for the period of from 15 minutes to 20 hours.

* * * * *